United States Patent
Hosono et al.

(10) Patent No.: US 7,696,386 B2
(45) Date of Patent: Apr. 13, 2010

(54) METHOD OF PRODUCING DIOL, POLYDIOL, SECONDARY ALCOHOL OR DIKETONE COMPOUND

(75) Inventors: Hideo Hosono, Kanagawa (JP); Haritha Buchammagari, Tokyo (JP); Yoshitake Toda, Saitama (JP); Masahiro Hirano, Tokyo (JP); Kohtaro Osakada, Kanagawa (JP); Daisuke Takeuchi, Kanagawa (JP)

(73) Assignee: Japan Science and Technology Agency, Kawaguchi-shi (JP)

(*) Notice: Subject to any disclaimer, the term of this patent is extended or adjusted under 35 U.S.C. 154(b) by 0 days.

(21) Appl. No.: 12/441,780

(22) PCT Filed: Sep. 28, 2007

(86) PCT No.: PCT/JP2007/069100

§ 371 (c)(1),
(2), (4) Date: Mar. 18, 2009

(87) PCT Pub. No.: WO2008/038801

PCT Pub. Date: Apr. 3, 2008

(65) Prior Publication Data

US 2009/0240085 A1    Sep. 24, 2009

(30) Foreign Application Priority Data

Sep. 29, 2006   (JP) .............. 2006-268796
Mar. 7, 2007   (JP) .............. 2007-056820

(51) Int. Cl.
*C07C 45/00* (2006.01)
*C07C 31/18* (2006.01)
*C07C 29/16* (2006.01)

(52) U.S. Cl. .............. 568/315; 568/363; 568/862; 568/903

(58) Field of Classification Search .............. 568/315, 568/363, 862, 903
See application file for complete search history.

(56) References Cited

U.S. PATENT DOCUMENTS

2005/0279279 A1   12/2005   Hosono et al.

2006/0151311 A1   7/2006   Hosono et al.

FOREIGN PATENT DOCUMENTS

| EP | 1961702 A1 | 8/2008 |
|---|---|---|
| JP | 4-300971 A | 10/1992 |
| JP | 10-87530 A | 4/1998 |
| JP | 2002-265391 A | 9/2002 |
| JP | 2002-332252 A | 11/2002 |
| JP | 2004-26608 A | 1/2004 |
| WO | 03/089373 A1 | 10/2003 |
| WO | 2005/000741 A1 | 1/2005 |
| WO | 2007/060890 A1 | 5/2007 |

OTHER PUBLICATIONS

Y. Zasshi "Reactions of Anthrone and Its Derivatives Using Pyridine N-Oxide as Oxidizing Reagent," 1983; vol. 103; pp. 273-278. Chemical Abstracts; vol. 125; Abs. No. 167109.
H. Buchammagari "Room Temperature-Stable Electride as a Synthetic Organic Reagent: Application to Pinacol Coupling Reaction in Aqueous Media," Organic Letters 2007; vol. 9; No. 21; pp. 4287-4289.
G. M. Robertson "Pinacol Coupling Reactions," Organic Synthesis 3; 1991; pp. 563-611.
H. B. Bartl "Zur Struktur des 12CaO·7Al2O3," Mineral Monatsh; 1970; vol. 35; pp. 547-552.
F.J. Tehan "Alkali Anions. Preparation and Crystal Structure of a Compound Which Contains the Cryptated Sodium Cation and the Sodium Anion," J. Am. Chem. Socity; 1974; vol. 96; pp. 7203-7208.
S. Matsuishi "High-Density Electron Anions in a Nanoporous Single Crystal: [Ca24Al28O64]4+(4e-)," Science; 2003; vol. 301; No. 5633; pp. 626-629.
International Search Report of PCT/JP2007/069100, date of mailing Dec. 18, 2007.

*Primary Examiner*—Sikarl A Witherspoon
(74) *Attorney, Agent, or Firm*—Westerman, Hattori, Daniels & Adrian, LLP

(57) ABSTRACT

The invention is a process of using, as a reducing agent, a $12CaO.7Al_2O_3$ electride containing electrons in a number of $10^{19}$ or more and $2.3 \times 10^{21}$ cm$^{-3}$ or less in its cages to subject a carbonyl compound to reductive coupling in a solvent, thereby synthesizing a diol or polydiol. The invention is also a process of reducing a ketone compound in a solvent, thereby synthesizing a secondary alcohol or diketone compound. According to the process of the invention, it is possible to synthesize a diol or polydiol, or a secondary alcohol or diketone compound through simple operations in a short period without using an expensive and harmful metal hydride or metal salt nor limiting the atmosphere for the synthesis to an inert gas atmosphere as in conventional processes.

15 Claims, No Drawings

METHOD OF PRODUCING DIOL, POLYDIOL, SECONDARY ALCOHOL OR DIKETONE COMPOUND

TECHNICAL FIELD

The present invention relates to a process for producing a diol or polydiol, or a secondary alcohol or diketone compound by use of an $12CaO \cdot 7Al_2O_3$ electride as a reducing agent.

BACKGROUND ART

About the synthesis of a diol by reductive coupling reaction of a carbonyl compound, it is known that a metal compound or metal salt, such as magnesium amalgam, aluminum amalgam, samarium iodide or vanadium chloride, functions as a reducing agent (Non-Patent Document 1).

However, the metal compound or metal salt is expensive and harmful, and further it is necessary to conduct the reaction in a water-free organic solvent in the atmosphere of an inert gas. For this reason, the reaction using the metal compound or metal salt was very unsatisfactory for a simple and environment-friendly reducing process. Known is also a process of conducting the reaction in an organic solvent, using metallic calcium as a reducing agent (Patent Document 1).

Secondary alcohols and diketones containing an aryl group and/or an alkyl group are widely used as intermediate compounds for medical supplies, colorants, and others. It is necessary to synthesize these compounds by an environment-friendly and safe process.

For the synthesis of a secondary alcohol through reductive reaction of a ketone compound, it is known that a metal hydride containing boron or aluminum, such as $NaBH_4$, $LiBH_4$, $LiAlH_4$ or $Zn(BH_4)_2$, functions as a reducing agent. However, the metal hydride is expensive and harmful, and further these metal hydride has a drawback that the metal hydride can be used only in a dry atmosphere and a dry solvent containing no water since the metal hydride dislikes the presence of water extremely. Besides, known is a process of causing polymethylhydrosiloxane to react with a ketone in the presence of a catalytic amount of tetrabutylammonium fluoride to reduce the carbonyl group of the ketone, thereby yielding an alcohol compound (Patent Document 2).

In 1970, H. B. Bartl et al. disclosed that the crystal of $12CaO \cdot 7Al_2O_3$ (referred to as "C12A7") has a unique crystal structure that two out of 66 oxygen ions present in a cell containing two molecules thereof undergo clathration, as "free oxygen", into spaces in cages present in the crystal (Non-Patent Document 2). Thereafter, it was made evident that the free oxygen ions can be substituted with various anions. In particular, when C12A7 is held in an intensely reducing atmosphere, entire free oxygen can be substituted with electrons. $C12A7:e^-$, wherein free oxygen is substituted with electrons, can be regarded as an electride.

Electride compounds are based on an idea suggested unprecedentedly by J. L. Dye (Non-Patent Document 3). No electride compounds were realized until a compound containing a crown ether as a cation and an electron as an anion, and other compounds were produced. It is known that an electride exhibits electroconductivity through the hopping of an electron contained as an anion. Thereafter, some organic electrides were found out. However, all of these compounds are stable only at a temperature as low as about $-100°$ C. or lower, and are remarkably unstable compounds reactive with air or water.

The inventors filed, as a patent application, an invention relating to electroconductive C12A7 and analogue compounds thereof, and a production process thereof (Patent Document 3). The inventors found out that a C12A7 compound having an electroconductivity of $10^3$ S/cm or less is yielded by annealing C12A7 monocrystal at high temperature in a vapor of an alkali metal or alkaline earth metal, ion-implanting an inactive ion such as Ar into C12A7 monocrystal, or solidifying C12A7 monocrystal directly from a melt in a reducing atmosphere. An invention relating thereto was filed as a patent application (Patent Document 4). Furthermore, the inventors succeeded in yielding C12A7 exhibiting metallic electroconductivity by annealing C12A7 monocrystal in a vapor of metallic titanium (Ti), and then filed, as a patent application, the production process of C12A7, and a usage thereof as an electron-releasing material (Patent Document 5).

These C12A7 compounds, which exhibit a good electroconductivity, are compounds wherein all of free oxygen ions are substituted with electrons, are each substantially represented by $[Ca_{24}Al_{28}O_{64}]^{4+} (4e^-)$, and can be regarded as inorganic electride compounds (Non-Patent Document 4).

Electrons undergoing clathration into C12A7 electrides are loosely bonded to cations, so that the electrons can be taken into the outside by applying an electric field thereto or by a chemical means. It appears that the electrons taken into the outside can be used in reductive reaction. However, unknown is an example in which electrons undergoing clathration into a C12A7 electride are applied directly to reductive reaction.

Non-Patent Document 1: G. M. Robertson, Comprehensive Organic Synthesis 3, 563 (1991)

Non-Patent Document 2: H. B. Bartl, T, Scheller and N. Jarhrb, Mineral Monatsh, 1970, 35, 547-552

Non-Patent Document 3: F. J. Tehan, B. L. Barrett, J. L. Dye, J. Am. Chem. Society, 96, 7203-7208 (1974)

Non-Patent Document 4: S. Matsuishi, Y. Toda, M. Miyakawa, K. Hayashi, T. Kamiya, M, Hirano, I. Tanaka and H. Hosono, Science, 301, 626-629 (2003)

Patent Document 1: Japanese Patent Application Laid-Open (JP-A) No. 2002-265391

Patent Document 2: JP-A No. 10-87530

Patent Document 3: WO 2005/000741A1

Patent Document 4: JP-A No. 2004-26608

Patent Document 5: WO 2007/060890A1

DISCLOSURE OF THE INVENTION

Problems to be solved by the invention

An object of the invention is to provide a novel reductive reaction for synthesizing a diol or polydiol by use of a carbonyl compound as a raw material or synthesizing a secondary alcohol or diketone compound by use of a ketone compound as a raw material without using an expensive and harmful metal hydride or metal salt for the synthesizing reaction nor limiting the atmosphere for the reaction to an inert gas atmosphere as in conventional processes.

Means for Solving the Problems

In order to attain the object, the inventors have been repeatedly made eager investigations, so as to find out that when a C12A7 electride, which exhibits electroconductivity, is used as a reducing agent, a reductive coupling reaction of a carbonyl compound or a reductive reaction of a ketone compound advances in water, an organic solvent, or a water/organic mixed solvent under the air also.

Accordingly, the invention is (1) a process for producing a diol or polydiol, comprising the step of using, as a reducing agent, a 12CaO.7Al$_2$O$_3$ electride containing electrons in a number of $10^{19}$ cm$^{-3}$ or more and $2.3 \times 10^{21}$ cm$^{-3}$ or less in its cages to subject a carbonyl compound to reductive coupling in water, an organic solvent, or a mixed solvent of water and an organic solvent.

The invention is also (2) the process for producing a diol or polydiol according to item (1), wherein the carbonyl compound is a compound wherein at least one out of two substituents bonded to a carbonyl group is an aryl group.

The invention is also (3) the process for producing a diol or polydiol according to item (1), wherein the carbonyl compound is represented by the following general formula:

[Chemical formula 1]

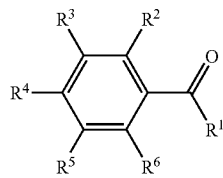

wherein R$^1$ is a functional group selected from a hydrogen atom, an alkyl group and an aryl group, R$^2$, R$^3$, R$^4$, R$^1$ and R$^6$ are each a functional group, bonded to the aryl group, selected from a hydrogen atom, a chloro group, a bromo group, an iodo group, an alkyl group, an aryl group, a carbonyl group, an allyl group, a vinyl group, an amino group, a hydroxy group, an alkoxy group, a nitro group, a cyano group, and an imino group, and R$^1$ and the aryl group may be bonded to each other to form a ring structure.

The invention is also (4) the process for producing a diol or polydiol according to item (1), wherein about the use amount of the 12CaO.7Al$_2$O$_3$ electride relative to the carbonyl compound (12CaO.7Al$_2$O$_3$/the carbonyl compound), the ratio by weight of the former to the latter is from 2 to 20.

The invention is also (5) the process for producing a diol or polydiol according to item (1), wherein a reaction atmosphere for the reductive coupling is in the air. [Definition of Carbonyl Compound]

In the invention, a carbonyl compound is defined as a compound wherein two substituents are bonded to a carbonyl group and the two substituents are each one selected from an alkyl group, an aryl group, and hydrogen. However, the compound wherein the two substituent are simultaneously hydrogen is not included therein.

[Definition of Diol]

In the invention, a diol is defined as a compound wherein a hydroxy group is bonded to each of two carbon atoms adjacent to each other. A polydiol is defined as a compound containing this diol structure and one or more diol structures equal thereto.

Furthermore, the invention is (6) a process for producing a secondary alcohol, comprising the step of using, as a reducing agent, a 12CaO.7Al$_2$O$_3$ electride containing electrons in a number of $10^{19}$ cm$^{-3}$ or more and $2.3 \times 10^{21}$ cm$^{-3}$ or less in its cages to reduce a ketone compound represented by the formula of compound in the following reaction equation 1 in water, an organic solvent, or a mixed solvent of water and an organic solvent, thereby synthesizing the secondary alcohol which is a secondary alcohol represented by the formula of compound 2 in the reaction equation 1:

(reaction equation 1)

[Chemical formula 2]

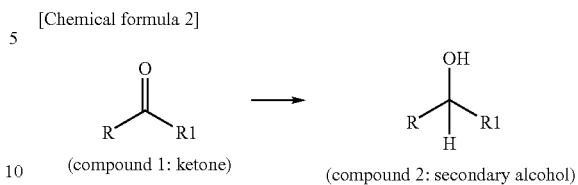

(compound 1: ketone)   (compound 2: secondary alcohol)

wherein R and R$^1$ are functional group selected from an aryl group and an alkyl group, and at least one of R and R$^1$ contains an aryl group.

The invention is also (7) a process for producing a dianthrone, comprising the step of using, as a reducing agent, a 12CaO.7Al$_2$O$_3$ electride containing electrons in a number of $10^{19}$ cm$^{-3}$ or more and $2.3 \times 10^{21}$ cm$^{-3}$ or less in its cages to dimerize an arylketone compound (anthrone) represented by the formula of compound 3 in the following reaction equation 2 in a mixed solvent of water and an organic solvent, thereby synthesizing the dianthrone which is a dianthrone represented by the formula of compound 4 in the reaction equation 2:

(reaction equation 2)

[Chemical formula 3]

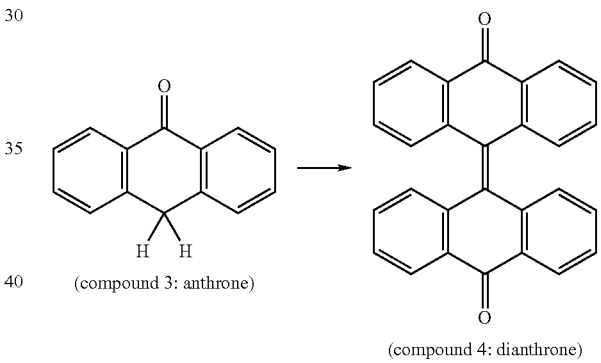

(compound 3: anthrone)   (compound 4: dianthrone)

Additionally, the invention is (8) a process for producing a dichalcone mixture, comprising the step of using, as a reducing agent, a 12CaO.7Al$_2$O$_3$ electride containing electrons in a number of 101 cm$^{-3}$ or more and $2.3 \times 10^{21}$ cm$^{-3}$ or less in its cages to dimerize a ketone compound represented by the formula of compound 5 in the following reaction equation 3 (chalcone), which contains a carbon double bond, in a mixed solvent of water and an organic solvent, thereby synthesizing dichalcones represented by the formulae of compound 6 and compound 7 in the reaction equation 3:

[Chemical formula 4]

(reaction equation 3)

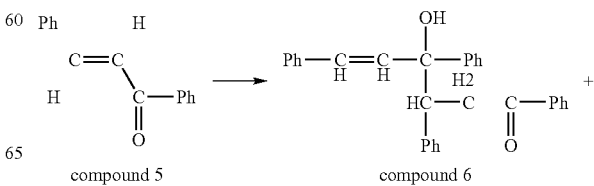

compound 5   compound 6

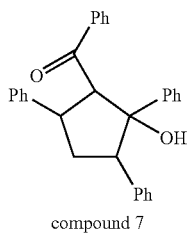

compound 7

[Definition of 12CaO.7Al$_2$O$_3$ (C12A7) Electride]

In the crystal structure of C12A7, 12 cages are present per its cell, which is composed of two molecules thereof, and oxygen ions (O$^{2-}$) undergo clathration into two of the cages. The oxygen ions can partially or wholly be substituted with electrons. When the oxygen ions are wholly substituted, the electron concentration is 2.3×10$^{21}$ cm$^{-3}$. In the invention, a compound wherein oxygen ions undergoing clathration therein are partially substituted with electrons (in a number of 1×10$^{19}$ cm$^{-3}$ or more and 2.3×10$^{21}$ cm$^{-3}$ or less), or are wholly substituted therewith (in a number of 2.3×10$^{21}$ cm$^{-3}$) is defined as a C12A7 electride (C12A7:e$^-$).

A C12A7 electride can be obtained by annealing C12A7 having a stoichiometric composition at about 700° C. in a metallic Ca vapor or annealing C12A7 having a stoichiometric composition at about 1100° C. in a metallic Ti vapor. The electron concentration in C12A7 becomes larger in accordance with the increase in annealing time.

In the case of treating in the metallic Ti vapor, a C12A7 electride having a theoretical maximum electron concentration (2.3×10$^{21}$ cm$^{-3}$) can be obtained by the annealing for about 24 hours, even if C12A7 is monocrystal of 3 mm thickness. Also a C12A7 melt having a stoichiometric composition may be solidified in a reducing atmosphere. The concentration of the C12A7 electride obtained by the solidification in the reducing atmosphere is 10$^{21}$ cm$^{-3}$ or less. A C12A7 electride can be prepared also by ion-implanting Ar$^+$ ions into a high concentration in C12A7. The electron concentration in the resultant C12A7 electride can be obtained based on the intensity of the optical band, which has a peak at 2.8 eV. When the electron concentration is small, the electron concentration can be obtained also based on the intensity of the electron spin resonance absorption band.

ADVANTAGEOUS EFFECTS OF THE INVENTION

According to the process of the invention, it is possible to synthesize a diol or polydiol from a carbonyl compound as a raw material or synthesize a secondary alcohol or diketone compound from a ketone compound as a raw material through simple operations in a short period without using an expensive and harmful metal hydride or metal salt for the synthesizing reaction nor limiting the atmosphere for the reaction to an inert gas atmosphere as in conventional processes.

BEST MODE FOR CARRYING OUT THE INVENTION

A C12A7 electride used as a reducing agent may be in the form of powder, a solid sintered body or a solid crystal, or in any other form. About the powdery C12A7 electride, it is advisable to anneal C12A7 powder having a stoichiometric composition in a metallic Ca vapor or a metallic Ti vapor. About the C12A7 electride in the form of a solid sintered body, it is advisable to solidify a C12A7 melt having a stoichiometric composition in a reducing atmosphere. About the C12A7 electride in the form of a solid monocrystal, it is advisable to anneal a C12A7 monocrystal in a metallic Ca vapor or a metallic Ti vapor. In order to make the reductive reaction rate larger, it is most suitable to convert a solid sample into powder. For the powdering process, pulverization in a mortar, pulverization by use of a jet mill, or the like may be used.

<Process for Reducing Carbonyl Compound>

The carbonyl-compound-reducing process of the invention will be described in detail hereinafter.

The carbonyl-compound-reducing process of the invention is a process of using, as a reducing agent, a 12CaO.7Al$_2$O$_3$ electride containing electrons in a number of 10$^{19}$ cm$^{-3}$ or more and 2.3×10$^{21}$ cm$^{-3}$ or less in its cages to subject a carbonyl compound to reductive coupling in a solvent. In the of using, for example, benzaldehyde as the carbonyl compound, 1,2-diphenyl-1,2-ethanediol can be produced by a reductive coupling reaction by the following equation:

[Chemical formula 5]

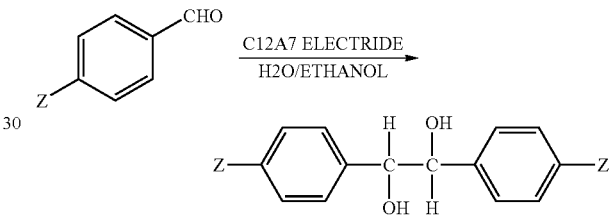

The invention can be applied to a carbonyl compound. Example of the carbonyl compound represented by the general formula illustrated above include 1-naphthoaldehyde, 2-naphthoaldehyde, 1-bromo-2-naphthoaldehyde, 2-hydroxy-1-naphthoaldehyde, 1-hydroxy-2-naphthoaldehyde, 2-methoxy-1-naphthoaldehyde, 1-methoxy-2-naphthoaldehyde, 6-methoxy-2-naphthoaldehyde, 1-nitro-2-naphthoaldehyde, 2,3-dimethoxy-1-naphthoaldehyde, 4-hydroxy-1-naphthoaldehyde, and 2,3-naphthalenedialdehyde, or the like.

Examples of a compound wherein R$^1$ is H out of the carbonyl compounds represented by the general formula illustrated above include benzaldehyde, 4-methylbenzaldehyde, 4-ethylbenzaldehyde, 4-t-butylbenzaldehyde, 4-chlorobenzaldehyde, 4-methoxybenzaldehyde, 2-nitrobenzaldehyde, 3-nitrobenzaldehyde, 4-hydroxybenzaldehyde, 4-cyanobenzaldehyde, 4-ethoxycarbonylbenzaldehyde, 2,4-dimethoxybenzaldehyde, 4-bromobenzaldehyde, 4-octyloxybenzaldehyde, 4-dimethylaminobenzaldehyde, and 2-hydroxybenzaldehyde, or the like.

As the solvent, the following may be used: water; an organic solvent, such as an alcohol such as methanol, ethanol or propanol, an ether such as tetrahydrofuran, dioxane or diethyl ether, chloroform, methylene chloride, benzene, toluene, N,N-dimethylformamide, or dimethylsulfoxide; a mixed organic solvent of two or more thereof; or a water/organic mixed solvent. From the viewpoint of the environment, only water or an organic mixed solvent containing water is most preferred. If the ratio by volume of the organic solvent (organic solvent/(water+organic solvent)) becomes larger, the reaction rate becomes smaller. The ratio is desirably 0 or more and less than 80.

About the use amount of the C12A7 electride relative to the carbonyl compound (C12A7/the carbonyl compound), the ratio by weight of the former to the latter is preferably from 2 to 20. If the ratio is less than 2, the reaction rate is small. If the ratio is 20 or more, the viscosity of the solution increases so that the solution is not easily stirred smoothly.

The atmosphere for the reaction is preferably the atmosphere of air having a pressure of 1 atm., and may be an inactive atmosphere. As the reaction temperature rises, the reaction rate increases. Practically, the temperature is most desirably room temperature. The temperature preferably ranges from 0° C. to 100° C. If the temperature is 0° C. or lower, water unfavorably freezes. If the temperature is 100° C., water unfavorably vaporizes so that the reaction does not advance. The reaction time depends on the kind of the carbonyl compound and the reaction temperature; however, the reaction ends completely in a time from 15 hours to 96 hours.

Under conditions as described above, the carbonyl compound and C12A7 are stirred and mixed in the solvent. Next, a product is extracted from the reaction solution in post-treatment. The method for the extraction may be a known method adopted as a method of extraction from a reaction solution. Specifically, for example, hydrochloric acid is added to the reaction solution, and then, for example, ethyl acetate is added thereto so as to extract the product. This extracting process is repeated about 3 times, and then the product is washed with sodium bicarbonate solution and sodium chloride solution. Thereto is added magnesium sulfate to dry the solution. Thereafter, magnesium sulfate is filtrated off, and the solvent is distilled off. The resultant is purified by column chromatography (silica gel). The finally produced compound can be separated by the chemical pre-treatment and the column chromatography. The identification of the compound and the rate of the conversion from the starting material can be obtained based on the $H^1$ nuclear magnetic resonance spectrum.

<Process for Reducing Ketone Compound>

The ketone-compound-reducing process of the invention will be described in detail hereinafter. The ketone-compound-reducing process of the invention is a process of using, as a reducing agent, a $12CaO \cdot 7Al_2O_3$ electride containing electrons in a number of $10^{19}$ cm$^{-3}$ or more and $2.3 \times 10^{21}$ cm$^{-3}$ or less in its cages to convert the carbonyl group C=O of a ketone compound to CH—OH in water, an organic solvent, or a mixed solvent of water and an organic solvent, thereby synthesizing a secondary alcohol. As the ketone compound, a compound 1 represented by the following formula is used:

[Chemical formula 6]

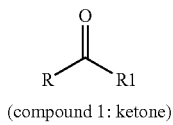

(compound 1: ketone)

R and $R^1$ are functional group selected from an aryl group and an alkyl group, and at least one of R and $R^1$ contains an aryl group. Preferably, R and $R^1$ are each one selected from a methyl group, a phenyl group, a phenylcyano group, or a phenylmethoxy group. However, a ketone compound wherein R and $R^1$ are simultaneously methyl groups is excluded. Specific examples thereof include p-cyanophenyl methyl ketone, di p-methoxyphenyl ketone, and diphenyl ketone, or the like. In the case of using, for example, p-cyanophenyl methyl ketone as the ketone compound, p-cyanophenyl methyl alcohol can be produced through reductive reaction.

The invention is also a process of using, as a reducing agent, a $12CaO \cdot 7Al_2O_3$ electride containing electrons in a number of $10^{19}$ cm$^{-3}$ or more and $2.3 \times 10^{21}$ cm$^{-3}$ or less in its cages to dimerize a ketone compound containing, besides the ketone group thereof, a different active group (such as a carbon double bond) in a solvent, thereby synthesizing a diketone.

As the ketone compound containing, besides the ketone group, a different active group, the following is used: an aryl ketone compound 3 represented by a formula illustrated below (anthrone; 9,10-dihydroanthracene-9-one), or a ketone compound 5 containing a carbon double bond (chalcone; benzylideneacetophenone). In the case of using anthrone or chalcone as the active-group-containing ketone compound, dianthrone or dichalcone can be produced.

[Chemical formula 7]

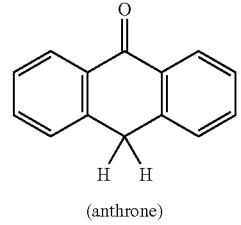

(anthrone)

[Chemical formula 8]

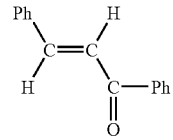

For an easily-reducible ketone compound, about 50% of electrons in C12A7 are used in the reductive reaction thereof. Therefore, a C12A7 electride having a higher electron concentration is more desirable. However, even an electride having a small electron concentration can cause a reductive reaction of a ketone when the charging amount thereof is increased. The electron concentration is from $10^{19}$ cm$^{-3}$ to $2.3 \times 10^{21}$ cm$^{-3}$, and is more preferably from $10^{20}$ cm$^{-3}$ to $2.3 \times 10^{21}$ cm$^{-3}$. The electron concentration of a C12A7 electride obtained directly by solidifying a melt in a reducing atmosphere is $10^{19}$ cm$^{-3}$ or more. This low-electron-concentration electride is also effective as a ketone-reducing agent.

In the production reaction of a secondary alcohol based on the reduction of a ketone, the following may be used as a solvent: water; an organic solvent, such as an alcohol such as methanol, ethanol or propanol, an ether such as tetrahydrofuran (THF), dioxane or diethyl ether, chloroform, methylene chloride, benzene, toluene, N,N-dimethylformamide, or dimethylsulfoxide; a mixed organic solvent of two or more thereof; or a mixed solvent of water and an organic solvent. From the viewpoint of the environment, only water or a mixed solvent of an organic solvent that contains water is preferred. If the ratio by volume of the organic solvent (organic solvent/(water+organic solvent)) becomes larger, the reductive reaction rate becomes smaller. The ratio is desirably 0 or more and 80 or less.

In the meantime, about the dimerization reaction of a ketone compound, the reaction does not advance in a solvent made only of water. Thus, a mixed solvent of water and an organic solvent are used. As the organic solvent, can be used $CH_3CN$, Et-OH, t-Bu-OH, dioxane, tetrahydrofuran (THF), or the like. In the dimerization reaction of anthrone, $CH_3CN$ is suitable since no byproduct is generated. In the dimerization reaction of chalcone, tetrahydrofuran (THF) is suitable since the yield is high.

In any one of the reductive reaction and the dimerization reaction of a ketone, about the use amount of the C12A7 electride relative to the ketone compound (C12A7/the ketone compound), the ratio by weight of the former to the latter is preferably from about 2 to 20. If the ratio is less than 2, the reductive reaction rate becomes small. If the ratio is more than 20, the viscosity of the solution increases so that the solution is not easily stirred smoothly. The ratio is more preferably from about 5 to 15. In the ketone-compound-reducing process of the invention, a catalyst is not particularly required since electrons contained in the C12A7 electride are released in the reductive reaction so that the electrons react with a ketone compound.

The pressure in the reductive reaction may be any one of normal pressure, increased pressure and reduced pressure. The reaction may be in the air, or in an inactive atmosphere. From the viewpoint of productivity, preferred is the atmosphere of the air having a pressure of 1 atm. About the reaction temperature, the reductive reaction rate becomes larger as the reaction temperature becomes higher. Thus, from the viewpoint of productivity, a high temperature is desirable. However, if the temperature is higher than 100° C., the yield is lowered by side reaction or the like; thus, the temperature is preferably 100° C. or lower. On the other hand, room temperature is desirable since reaction operations are easily conducted. If the temperature is lower than 0° C., water freezes. The temperature is preferably 25° C. or higher, and 100° C. or lower, more preferably 50° C. or higher, and 100° C. or lower. The reductive reaction time depends on the kind of the ketone compound, the reaction temperature and others; however, the reductive reaction ends completely in a time from about 15 hours to 96 hours.

According to the dimerization reaction of a ketone including an additional active group, a diketone can be produced also in the atmospheric air, which contains oxygen gas. In the atmospheric air, however, a byproduct wherein the active group is oxidized is produced. It is therefore preferred to use an inert gas atmosphere in order to synthesize a diketone compound selectively. The inert gas atmosphere is suitably a nitrogen gas atmosphere from the viewpoint of economy.

Preferably, a monocrystal C12A7 electride or polycrystal electride is pulverized into powder having an average particle diameter of about 10 μm in a mortar to prepare reductant. The powder is added to a ketone compound, and the components are stirred and mixed in a solvent under conditions described above. Next, in post-treatment, a product is extracted from the reaction solution. The method for the extraction may be a known method adopted as a method for extraction from a reaction solution.

Specifically, for example, hydrochloric acid is added to the reaction solution, and then, for example, ethyl acetate is added thereto so as to extract the product. This extracting process is repeated about 3 times, and then the product is washed with sodium bicarbonate solution and sodium chloride solution. Thereto is added magnesium sulfate to adsorb water, thereby removing water. Next, magnesium sulfate is filtrated off, and the solvent is distilled off. The resultant is purified by column chromatography (silica gel). The finally produced compound can be separated by the chemical pre-treatment and the column chromatography. The identification of the compound and the rate of the conversion from the raw material can be obtained based on the $H^1$ nuclear magnetic resonance spectrum.

The conversion rate of the dimerization reaction of the ketone depends on the kind of the solvent, and the kind of the gas of the reaction atmosphere, and ranges from about 40 to 60%. Whether or not a byproduct is produced, and the chemical structure thereof also depend on the kind of the solvent, and the kind of the gas of the reaction atmosphere. For example, in the reaction of dimerizing anthrone to produce dianthrone, only dianthrone is produced without producing any byproduct when the reaction is conducted in a dry nitrogen atmosphere, using cyanomethane as a solvent. However, when the reaction is conducted in the air, anthraquinone, which is obtained by oxidizing anthrone and is represented by formula [9] illustrated below, is produced with a conversion rate of about 30%. When dioxane is used as the solvent, a byproduct wherein anthrone and dioxane are bonded to each other, which is represented by formula [10] illustrated below, is produced with a conversion rate of about 20%.

[Chemical formula 9]

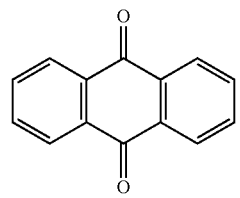

[Chemical formula 10]

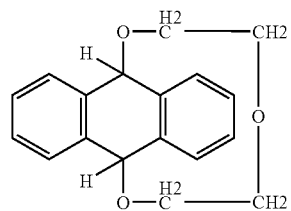

The invention will be described in more detail by way of the following examples:

(Preparation of a C12a7 Electride)

Prepared was a C12A7 electride having an electron concentration of about $2 \times 10^{21}$ cm$^{-3}$ was prepared. This C12A7 electride was produced by the following method: From a C12A7 monocrystal ingot produced by the Czochralski method, a plate, mm×10 mm×3 mm, was cut out, and then the plate together with metallic Ti was put into a quartz tube so as to seal the tube in a vacuum. The quartz tube is put into an electric furnace, kept at 1100° C. for 24 hours, and then cooled with the air. The electron concentration of the resultant C12A7 electride was obtained by converting the light reflection spectrum of the electride to an optical absorption spectrum and then measuring the intensity of the 2.8-eV absorption band thereof. This monocrystal C12A7 electride was pulverized in a mortar to yield powder having an average particle diameter of about 10 μm.

<Production of Diols or Polydiols>

Examples 1 to 14

TABLE 1

| Example No. | Carbonyl compound *① | C12A7 electride amount mg (electron concentration: $cm^3$) | Solvent (volume: ml) | Reaction time (h) | Reaction temperature (° C.) | Conversion rate (%) |
| --- | --- | --- | --- | --- | --- | --- |
| 1 | Benzaldehyde | 100 ($2 \times 10^{21}$) | Water (2) | 15 | 25 | More than 95 |
| 2 | " | 50 ($2 \times 10^{21}$) | Water (1) | 15 | 25 | More than 95 |
| 3 | " | 200 ($2 \times 10^{21}$) | *② (4) | 24 | 90 | More than 95 |
| 4 | 4-Methylbenzaldehyde | 131 ($2 \times 10^{21}$) | Water (4) | 19 | 25 | More than 95 |
| 5 | 4-Ethylbenzaldehyde | 121 ($2 \times 10^{21}$) | Water (4) | 19 | 25 | More than 95 |
| 6 | " | 30 ($2 \times 10^{21}$) | Water (1) | 30 | 25 | More than 95 |
| 7 | 4-t-Butylbenzaldehyde | 98 ($2 \times 10^{21}$) | Water (4) | 16 | 100 | More than 95 |
| 8 | 4-Chlorobenzaldehyde | 117 ($2 \times 10^{21}$) | Water (4) | 22 | 100 | More than 95 |
| 9 | 4-Methoxybenzaldehyde | 120 ($2 \times 10^{21}$) | Water (2) | 72 | 100 | More than 95 |
| 10 | " | 120 ($2 \times 10^{21}$) | Water (4) | 20 | 100 | 50 |
| 11 | 2-Nitrobenzaldehyde | 55 ($2 \times 10^{21}$) | Water (2) | 21 | 80 | 73 |
| 12 | 3-Nitrobenzaldehyde | 55 ($2 \times 10^{21}$) | Water (2) | 22 | 80 | 93 |
| 13 | 4-Hydroxybenzaldehyde | 66 ($2 \times 10^{21}$) | Water (2) | 27 | 25 | 16 |
| 14 | 4-Cyanobenzaldehyde | 62 ($2 \times 10^{21}$) | Water (2) | 22 | 25 | 60 |
| 15 | Benzaldehyde | 55 ($2 \times 10^{19}$) | Water (40) | 96 | 25 | More than 95 |

*① 10 mg in Examples 1 to 14, and 26 mg in Example 15
*② Water:ethanol = 1:4

Into an eggplant type flask 10 mL in volume were put 10 mg of each carbonyl compound described in Table 1, and further put the C12A7 electride and each solvent in respective amounts shown in Table 1. In the state that the inside thereof was open to the atmosphere, the active components were caused to react with each other at each reaction temperature shown in Table 1 for each reaction time shown therein while the solution was stirred. In this way, a reaction solution was prepared.

Next, the reaction solution was transferred to an eggplant type flask 50 mL in volume, and hydrochloric acid (1 N, 7 mL) was added thereto. Thereafter, thereto was added ethyl acetate (20 mL) and then the product was extracted. This extracting process was repeated 3 times, and then the product was washed with sodium bicarbonate solution and sodium chloride solution. Thereto was added magnesium sulfate to dry the solution. Thereafter, magnesium sulfate was filtrated off, and the solvent was distilled off. The resultant was purified by column chromatography (silica gel) to yield a diol compound having a purity of more than 98%. The identification of the compound was attained through the $H^1$ nuclear magnetic resonance spectrum thereof. The product of each of Examples is shown in Table 2. The conversion rate thereof (decrease rate of the carbonyl compound as the starting raw material) is as shown in Table 1.

TABLE 2

| Example No. | Produced compound |
| --- | --- |
| 1 | 1,2-Diphenyl-1,2-ethandiol |
| 2 | 1,2-Diphenyl-1,2-ethandiol |

TABLE 2-continued

| Example No. | Produced compound |
| --- | --- |
| 3 | 1,2-Diphenyl-1,2-ethandiol |
| 4 | 1,2-Bis(4-methylphenyl)-1,2-ethandiol |
| 5 | 1,2-Bis(4-ethylphenyl)-1,2-ethandiol |
| 6 | 1,2-Bis(4-ethylphenyl)-1,2-ethandiol |
| 7 | 1,2-Bis(4-t-butylphenyl)-1,2-ethandiol |
| 8 | 1,2-Bis(4-chlorophenyl)-1,2-ethandiol |
| 9 | 1,2-Bis(4-methoxyphenyl)-1,2-ethandiol |
| 10 | 1,2-Bis(4-methoxyphenyl)-1,2-ethandiol |
| 11 | 1,2-Bis(2-nitrophenyl)-1,2-ethandiol |
| 12 | 1,2-Bis(2-nitrophenyl)-1,2-ethandiol |
| 13 | 1,2-Bis(4-hydroxyphenyl)-1,2-ethandiol |
| 14 | 1,2-Bis(4-cyanophenyl)-1,2-ethandiol |
| 15 | 1,2-Diphenyl-1,2-ethandiol |

Example 15

A C12A7 electride having an electron concentration of $1 \times 10^{19}$ $cm^{-3}$ was produced by the following method: C12A7 powder was put in a carbon crucible with a cover. The powder was heated to 1600° C. in the atmosphere so as to be melted. The melt was cooled at a lowering rate of about 400° C./hour to yield polycrystal C12A7. The electron concentration was obtained based on the electron spin resonance spectrum. This polycrystal C12A7 electride was pulverized in a mortar to yield powder having an average particle diameter of about 10 μm.

In the same way as in Example 1 except that this electride was used, a reaction was conducted under conditions shown in Table 1. However, the amount of benzaldehyde was set to 25 mg. The product was 1,2-diphenyl-1,2-ethanediol, and the conversion rate was more than 95%. This result demonstrated that a reductive coupling reaction of a carbonyl compound occurred even when a C12A7 electrode having a small electron concentration is used.

Comparative Example 1

Reaction was conducted under the same conditions as in Example 1 shown in Table 1 except that C12A7 powder having a stoichiometric composition and containing no electrons was used instead of the C12A7 electrode. After the reaction, only benzaldehyde was detected, and no reductive coupling reaction was caused.

<Production of Secondary Alcohols or Diketone Compounds>

Example 16

Synthesis of a Secondary Alcohol

Into an eggplant type flask 10 mL in volume were put 10 mg of a ketone compound having R and R' groups of No. 1 as a raw material (compound 1) shown in Table 3, 196 mg of a C12A7 electrode, and 5 mL of a solvent (water:dioxane=1:4). In the state that the flask was open to the atmosphere, the active components were caused to react at a reaction temperature shown in Table 3 for a reaction time shown therein while the solution was stirred. Thus, a reaction solution was prepared.

was washed with sodium bicarbonate solution and sodium chloride solution. Thereto was added magnesium sulfate to adsorb water, thereby removing water. Next, magnesium sulfate was filtrated off, and the solvent was distilled off. The resultant was purified by column chromatography (silica gel) to yield a compound having a purity of more than 98%. The identification of the compound was attained through the $H^1$ nuclear magnetic resonance spectrum thereof. The product (compound 2) is shown in Table 4. The compound was a secondary alcohol represented by the formula of $RR^1HC-OH$ in Table 4. The yield of the purified secondary alcohol was 59%.

Example 17

Reaction was conducted under the same conditions as in Example 16 except that a ketone compound having R and $R^1$ groups of No. 2 in Table 3 was used as a raw material (compound 1), and the amount of the electride and the reaction time were set as shown in Table 3. In this way, a secondary alcohol represented by the formula of $RR^1HC-OH$ in Table 4 was yielded. The yield was 3%.

Example 18

Reaction was conducted under the same conditions as in Example 16 except that a ketone compound having R and $R^1$ groups of No. 3 in Table 3 was used as a raw material (compound 1), and the amount of the electride and the reaction time were set as shown in Table 3. In this way, a secondary

TABLE 3

Raw material (compound 1)

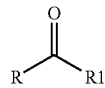

| | R | R1 | Electride (mg) | Solvent | Reaction time | Reaction temperature |
|---|---|---|---|---|---|---|
| 1 | Ph-p-CN(p-cyanophenyl) | CH3(methyl) | 196 | H2O/dioxane | 9 hours | 100° C. |
| 2 | Ph-p-OMe(p-methoxyphenyl) | Ph-p-OMe(p-methoxyphenyl) | 229 | H2O/dioxane | 17 hours | 100° C. |
| 3 | Ph(phenyl) | Ph(phenyl) | 164 | H2O/dioxane | 10 hours | 100° C. |

TABLE 4

Product (compound 2)

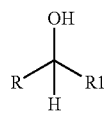

| | R | R1 | Yield |
|---|---|---|---|
| 1 | Ph-p-CN(p-cyanophenyl) | CH3(methyl) | 59% |
| 2 | Ph-p-OMe(p-methoxyphenyl) | Ph-p-OMe(p-methoxyphenyl) | 3% |
| 3 | Ph(phenyl) | Ph(phenyl) | 57% |

Next, the reaction solution was transferred to an eggplant type flask 50 mL in volume, and hydrochloric acid (1 N, 7 mL) was added thereto. Thereafter, thereto was added ethyl acetate (20 mL) and then the product was extracted. This extracting process was repeated 3 times, and then the product alcohol represented by the formula of $RR^1HC-OH$ in Table 4 was yielded. The yield was 57%.

Example 19

Synthesis of Dianthrone

Into a mixed solvent of water and cyanomethane (1:4) were put 10 mg of anthrone, and 164 mg of a C12A7 electride, and then the solution was put into an eggplant type flask 10 mL in volume. In the atmosphere of nitrogen gas, the active components were caused to react at 100° C. for 12 hours while the solution was stirred.

Next, the reaction solution was transferred to an eggplant type flask 50 mL in volume, and hydrochloric acid (1 N, 7 mL) was added thereto. Thereafter, thereto was added ethyl acetate (20 mL) and then the product was extracted. This extracting process was repeated 3 times, and then the product was washed with sodium bicarbonate solution and sodium chloride solution. Thereto was added magnesium sulfate to adsorb water, thereby removing water. Next, magnesium sulfate was filtrated off, and the solvent was distilled off. The resultant was purified by column chromatography (silica gel) to yield a compound having a purity of more than 98%. The identification of the compound was attained through the $H^1$ nuclear magnetic resonance spectrum thereof. The compound was dianthrone. The yield of the product was 45%, which was calculated from the weight of the product.

Example 20

Synthesis of Dichalcone

Into a mixed solvent of water and THF (1:4) were put 100 mg of chalcone, and 1200 mg of a C12A7 electride, and then the solution was put into an eggplant type flask 10 mL in volume. In the atmosphere of nitrogen gas, the active components were caused to react at 25° C. for 18 hours while the solution was stirred. In this way, a reaction solution was papered.

Next, the reaction solution was transferred to an eggplant type flask 50 mL in volume, and hydrochloric acid (1 N, 7 mL) was added thereto. Thereafter, thereto was added ethyl acetate (20 mL) and then the product was extracted. This extracting process was repeated 3 times, and then the product was washed with sodium bicarbonate solution and sodium chloride solution. Thereto was added magnesium sulfate to adsorb water, thereby removing water. Next, magnesium sulfate was filtrated off, and the solvent was distilled off. The resultant was purified by column chromatography (silica gel) to yield compounds. The identification of the compounds was attained through the $H^1$ nuclear magnetic resonance spectra thereof. The compounds were a mixture of dichalcones represented by the formula of compound 6 and compound 7. The yield of the compound 6 was 5% and that of the compound 7 was 23%, which were each calculated from the weight of the product.

Comparative Example 2

Reaction was conducted under the same conditions as in Example 16 except that C12A7 powder having a stoichiometric composition and containing no electrons was used instead of the C12A7 electride. After the reaction, only the ketone compound was detected, and no reductive reaction was caused.

INDUSTRIAL APPLICABILITY

The invention provides a process for synthesizing a secondary alcohol or diketone, or a diol or polydiol, which is used as an intermediate compound for medicine, or the like, with a high yield in a short time. The reaction therefore is a reaction that does not need any catalyst, such as a heavy metal, and is conducted in an aqueous solvent or a mixed solvent of water and an organic solvent. Thus, provided is a safe and environment-friendly synthesizing process for which no harmful material is necessary. Provided is also an inexpensive synthesizing process since the reaction can be attained at room temperature in the atmosphere.

The invention claimed is:

1. A process for producing a diol or polydiol, comprising the step of using, as a reducing agent, a 12CaO.7Al$_2$O$_3$ electride containing electrons in a number of $10^{19}$ cm$^{-3}$ or more and $2.3 \times 10^{21}$ cm$^{-3}$ or less in its cages to subject a carbonyl compound to reductive coupling in water, an organic solvent, or a mixed solvent of water and an organic solvent.

2. The process for producing a diol or polydiol according to claim 1, wherein the carbonyl compound is a compound wherein at least one out of two substituents bonded to a carbonyl group is an aryl group.

3. The process for producing a diol or polydiol according to claim 1, wherein the carbonyl compound is represented by the following general formula:

[Chemical formula 1]

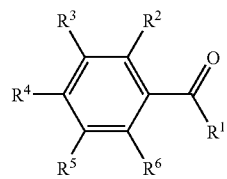

wherein $R^1$ is a functional group selected from a hydrogen atom, an alkyl group and an aryl group, $R^2$, $R^3$, $R^4$, $R^5$ and $R^6$ are each a functional group, bonded to the aryl group, selected from a hydrogen atom, a chloro radical, a bromo radical, a iodo radical, an alkyl group, an aryl group, a carbonyl group, an allyl group, a vinyl group, an amino group, a hydroxy group, an alkoxy group, a nitro group, a cyano group, and an imino group, and $R^1$ and the aryl group may be bonded to each other to form a ring structure.

4. The process for producing a diol or polydiol according to claim 1, wherein about the use amount of the 12CaO.7Al$_2$O$_3$ electride relative to the carbonyl compound (12CaO.7Al$_2$O$_3$/ the carbonyl compound), the ratio by weight of the former to the latter is from 2 to 20.

5. The process for producing a diol or polydiol according to claim 1, wherein a reaction atmosphere for the reductive coupling is the inside of air.

6. A process for producing a secondary alcohol, comprising the step of using, as a reducing agent, a 12CaO.7Al$_2$O$_3$ electride containing electrons in a number of $10^{19}$ cm$^{-3}$ or more and $2.3 \times 10^{21}$ cm$^{-3}$ or less in its cages to reduce a ketone compound represented by compound 1 in the following reaction equation 1 in water, an organic solvent, or a mixed solvent of water and an organic solvent, thereby synthesizing the secondary alcohol which is a secondary alcohol represented by compound 2 in the reaction equation 1:

(reaction equation 1)

[Chemical formula 2]

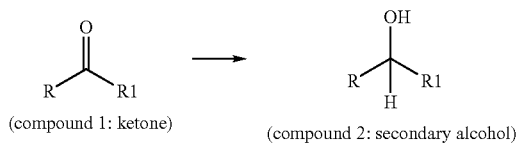

wherein R and $R^1$ are each a functional group selected from an aryl group and an alkyl group, and at least one of R and $R^1$ contains an aryl group.

7. The process for producing a secondary alcohol according to claim 6, wherein R and $R^1$ are each at least one selected from a methyl group, a phenyl group, a phenylcyano group, or a phenylmethoxy group, except that R and $R^1$ are simultaneously methyl groups.

8. The process for producing a secondary alcohol according to claim 6, wherein the organic solvent, or the organic solvent of the mixed solvent is dioxane.

9. The process for producing a secondary alcohol according to claim 6, wherein about the use amount of the $12CaO \cdot 7Al_2O_3$ electride relative to the ketone compound ($12CaO \cdot 7Al_2O_3$/the ketone compound), the ratio by weight of the former to the latter is from 2 to 20.

10. The process for producing a secondary alcohol according to claim 6, wherein an atmosphere for the reaction is the inside of the air.

11. A process for producing a dianthrone, comprising the step of using, as a reducing agent, a $12CaO \cdot 7Al_2O_3$ electride containing electrons in a number of $10^{19}$ cm$^{-3}$ or more and $2.3 \times 10^{21}$ cm$^{-3}$ or less in its cages to dimerize an arylketone compound (anthrone) represented by compound 3 in the following reaction equation 2 in a mixed solvent of water and an organic solvent, thereby synthesizing the dianthrone which is a dianthrone represented by compound 4 in the reaction equation 2:

(reaction equation 2)

[Chemical formula 3]

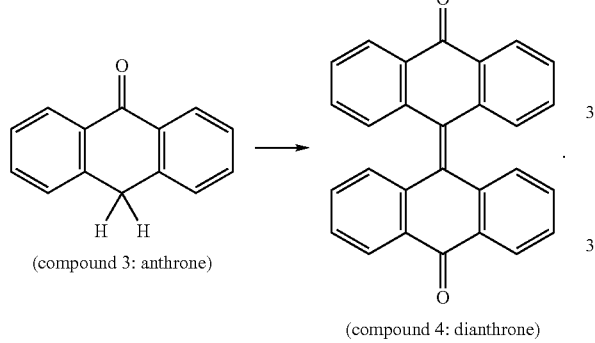

(compound 3: anthrone)

(compound 4: dianthrone)

12. The process for producing a dianthrone according to claim 11, wherein the organic solvent is selected from CH$_3$CN, Et-OH, t-Bu-OH, or dioxane.

13. The process for producing a dianthrone according to claim 11, wherein an atmosphere for the reaction is the inside of an inert gas.

14. A process for producing a dichalcone mixture, comprising the step of using, as a reducing agent, a $12CaO \cdot 7Al_2O_3$ electride containing electrons in a number of $10^{19}$ cm$^{-3}$ or more and $2.3 \times 10^{21}$ cm$^{-3}$ or less in its cages to dimerize a ketone compound represented by compound 5 in the following reaction equation 3 (chalcone), which contains a carbon double bond, in a mixed solvent of water and an organic solvent, thereby synthesizing dichalcones represented by compound 6 and compound 7 in the reaction equation 3:

(reaction equation 3)

[Chemical formula 4]

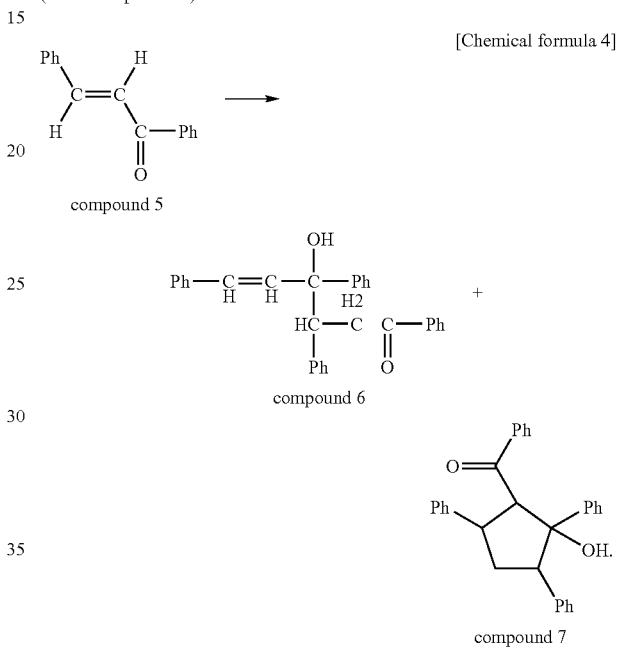

15. The process for producing a dichalcone according to claim 14, wherein the organic solvent is tetrahydrofuran (THF).

* * * * *